(12) United States Patent
Nishio et al.

(10) Patent No.: US 6,507,397 B1
(45) Date of Patent: Jan. 14, 2003

(54) AUTOMATIC COLOR-TONE TEST DEVICE AND AUTOMATIC CONTROLLING SYSTEM FOR DYE LIQUOR

(75) Inventors: Shigenori Nishio, Osaka (JP); Masao Kawakami, Osaka (JP); Hiroshi Kimura, Nara (JP); Kenji Muramoto, Osaka (JP)

(73) Assignee: Suminoe Textile Co., Ltd., Osaka (JP)

( * ) Notice: Subject to any disclaimer, the term of this patent is extended or adjusted under 35 U.S.C. 154(b) by 0 days.

(21) Appl. No.: 09/536,714

(22) Filed: Mar. 28, 2000

(30) Foreign Application Priority Data

Nov. 4, 1999 (JP) ............................................. 11-313487

(51) Int. Cl.$^7$ .................................................. G01J 3/42
(52) U.S. Cl. ....................... 356/319; 356/413; 356/440; 356/246
(58) Field of Search .................................... 356/319, 325, 356/323, 326, 328, 402, 410, 411, 413, 246, 440

(56) References Cited

U.S. PATENT DOCUMENTS

| 3,987,808 A | * | 10/1976 | Carbonell et al. .............. 137/3 |
| 4,374,322 A | * | 2/1983 | Hoffmann et al. .......... 356/411 |
| 5,780,602 A | * | 7/1998 | Schumacher et al. ....... 534/642 |

FOREIGN PATENT DOCUMENTS

| EP | 0631119 | 12/1994 |
| JP | 11-7323 | 1/1999 |
| JP | 11007323 | 2/1999 |

* cited by examiner

Primary Examiner—F. L. Evans
(74) Attorney, Agent, or Firm—Armstrong, Westerman & Hattori, LLP

(57) ABSTRACT

An automatic color-tone test device comprises: a measurement cell 4 to which there are communication-connected dye liquor introduction tubes 16, 18 for passing through a controlling dye liquor that is a measurement object and dye liquor discharge tubes 17, 19; a spectrophotometer adapted such that a light transmission distance in the measurement cell 4 can be variably set in compliance with a concentration level of the controlling dye liquor that is a measurement object; and a statistical test computer section for operation-judging whether or not concentration and hue agree with desired values.

6 Claims, 10 Drawing Sheets

: CONTROL FLOW RATE RANGE OF REGULATION VALVE

: DISCHARGE FLOW RATE RANGE OF PUMP

AUTOMATIC COLOR-TONE TEST DEVICE AND AUTOMATIC CONTROLLING SYSTEM FOR DYE LIQUOR

BACKGROUND OF THE INVENTION

1. Technical Field to Which the Invention Belongs

The present invention relates to an automatic color-tone test device capable of performing a color-tone test within a very short time for a measurement object dye liquor of any concentration over a very wide concentration range, and an automatic controlling system for dye liquor with a high accuracy, which has the automatic color-tone test device.

2. Related Art

In a field of dyeing textile products, in order to cope with a diversity in their designs, it is demanded to adjust a dye liquor with a high accuracy over a very wide concentration range from a low concentration to a high concentration and feed it to each feed tank. And, hitherto it has been performed by a so-called batch system in which powder dyes are precisely weighed, plural kinds of such dyes are dissolved into mixed states, and dye liquors each of which has been adjusted to a desired concentration are filled in each feed tank. However, with such a batch system, the more increases the number of variations in kinds and concentrations of the adjustment dye liquors in a multiple color dyeing the longer time is required for these controlling works, so that there has been a desired problem that a time required for the controlling works of the dye liquor should be reduced from an aspect of production efficiency.

Therefore, it has been desired to hastily develop an automatic controlling system for dye liquor, and as flow rate control means for making it possible to construct such an automatic controlling system that can adjust plural kinds of dye liquors with a high accuracy over a very wide concentration range from a low concentration to a high concentration and can feed them to each feed tank, the present applicant has previously proposed in Japanese Patent Application No. 9-161553 a flow rate control device comprising a main conduit having at its one end a suction port for taking in a fluid (dye mother liquor) and at its the other end a discharge port for the fluid, a pump provided in the main conduit and having a predetermined discharge flow rate range, a bypass conduit branched from a position of more discharge port side than the pump in the main conduit and reaching the discharge port, and flow meter and regulation valve which are provided in the bypass conduit, wherein a control flow rate range of the regulation valve contains a flow rate range of lower flow rate side than a predetermined discharge flow rate range of the pump and an opening adjustment of the regulation valve is performed on the basis of a measured value detected by the flow meter.

This flow rate control device can variably control the flow rate with a high accuracy over a wide flow rate range from a small flow rate to a large flow rate, so that if the flow rate control device having this constitution is incorporated into a feed line of each dye mother liquor, it is possible to discharge the dye mother liquor into a feed tube fed with water of constant flow rate while controlling it with a high accuracy over a wide flow rate range from a small flow rate to a large flow rate and, as a result, it becomes possible to adjust the dye liquor with a high accuracy over a very wide concentration range from a low concentration to a high concentration by using a single dye mother liquor, and to feed it.

As to the dye liquor thus controlled, it is necessary to check whether or not its concentration and hue agree with desired values, i.e. it is necessary to perform a color-tone test. In case where the controlling of the dye liquor by the above-mentioned conventional batch system, before the controlled dye liquor is filled in the feed tank, an absorbance of the controlling dye liquor is measured using a spectrophotometer and the color-tone test is performed using a known method called LCM (liquid color matching). And, in case where the controlling dye liquor has a high concentration, there has been adopted such a color-tone test method that the high concentration controlling dye liquor is diluted by water with a high accuracy such that it falls within a measurement range ability (generally, 0.001–0.05 g/L) of the spectrophotometer, i.e. such that it falls within a measurable concentration range, and an absorbance of the original controlling dye liquor is computed by measuring an absorbance of the dilution dye liquor.

By the way, since such an automatic controlling system as mentioned above is an on-line system in which the dye liquor is continuously fed from the dye mother liquor tank to the feed tank, it is desirable that the color-tone test of the controlling dye liquor is performed within a very short time (for example, in the order of several seconds) in compliance with the on-line system. That is, it is desirable that the color-tone test of the controlling dye liquor is performed within a very short time, results thereof is fed back and a fine adjustment of the controlling operation is executed as occasion demands.

However, if the color-tone test method similar to the prior art is adopted, this color-tone test requires about 5–6 minutes in case where the controlling dye liquor has an especially high concentration and a dilution operation is required. Since a long time is required in this manner, there has been no one which can become color-tone test means suitable for the automatic controlling system that is an on-line system. In other words, conventional color-tone test means could not so to speak continuously perform the color-tone test for the controlling dye liquor continuously being fed.

SUMMARY OF THE INVENTION

The invention was made in view of such a technical background, and objects of the invention are to provide an automatic color-tone test device capable of performing a color-tone test within a very short time for controlling dye liquor of any concentration over a very wide concentration range from a low concentration to a high concentration, and an automatic controlling system for dye liquor with a high accuracy, in which the automatic color-tone test device is used.

In order to achieve the above objects, as a result of intensive studies, the inventors found the fact that the above desired automatic color-tone test device can be obtained by adopting a constitution that makes it possible to introduce a controlling dye liquor that is a measurement object into a measurement cell in on-line through a tube and makes it possible to variably set a light transmission distance in the measurement cell in compliance with a concentration level of the controlling dye liquor that is a measurement object, and completed the invention.

That is, an automatic color-tone test device of the invention comprises: a spectrophotometer in which a dye liquor introduction tube for introducing a controlling dye liquor, that is a measurement object, into a measurement cell is communication-connected to the measurement cell, while a dye liquor discharge tube for discharging the dye liquor after having passed through the measurement cell is communication-connected to the measurement cell, and which is adapted such that a light transmission distance in the measurement cell can be variably set in compliance with a concentration level of the controlling dye liquor that is a measurement object; and a statistical test computer section for operation-judging whether or not the dye liquor's concentration and hue measured by the spectrophotometer agree with desired values.

Since it is adapted such that a light transmission distance in the measurement cell can be variably set in compliance with a concentration level of the controlling dye liquor that is a measurement object, in case where the concentration level of the controlling dye liquor is low for instance, the light transmission distance can be set large so as to fall within a measurement range ability of the spectrophotometer, and further in case where the concentration level of the controlling dye liquor is high, the light transmission distance can be set small so as to fall within a measurement range ability of the spectrophotometer, so that it is possible to perform the color-tone test within a very short time for controlling dye liquor of any concentration over a very wide concentration range from a low concentration to a high concentration. In comparison with a conventional system in which, in case where the dye liquor has a high concentration, a preliminary dilution process is required, a reduction in time required for the color-tone test is very remarkable, so that it is suitable as the color-tone test device in an automatic controlling system for dye liquor.

It is preferable that, in the automatic color-tone test device, an internal space of the measurement cell is divided into plural liquid-tight independent spaces mutually different in light transmission distance, and the dye liquor introduction tube and the dye liquor discharge tube are respectively communication-connected to each liquid-tight independent space, and it is so adapted that the controlling dye liquor is selectively fed to any one of the independent spaces in compliance with a concentration level of the controlling dye liquor that is a measurement object.

By the fact that it is so adapted that the controlling dye liquor is selectively fed to any one of the independent spaces in compliance with a concentration level of the controlling dye liquor that is a measurement object, it follows that the light transmission distance in the measurement cell is variably set in compliance with the concentration level of the controlling dye liquor and the light transmission distance in each independent space is non-variable and fixed, so that the light transmission distance at a time of measurement is maintained to a high accuracy even in case where any independent space is selected. For example, with such a constitution that an interval between opposed side walls of the measurement cell is variably controlled, it is difficult to control the light transmission distance with a high accuracy.

Further, an automatic controlling system for dye liquor of the invention comprises: an automatic controlling device having one or plural dye liquor tank(s) filled with dye liquor, a water tank filled with water, a mixer for mixing the liquor fed from each of the tanks, and one or plural flow rate control device(s) for controlling a flow rate of the liquor fed into the mixer from each of the tanks; an automatic color-tone test device set forth; and a control computer section which performs a component analysis on the basis of operation judgment results of the statistical test computer section of the automatic color-tone test device, and which is adapted so as to control the flow rate control device on the basis of the analysis results; wherein at least a part of the controlling dye liquor fed through the mixer of the automatic controlling device is introduced into the dye liquor introduction tube of the automatic color-tone test device.

Since the color-tone test is performed using the automatic color-tone test device of the above constitution, it is possible to perform the color-tone test within a very short time for controlling dye liquor of any concentration over a very wide concentration range from a low concentration to a high concentration, so that it is possible to perform a fine adjustment of the flow rate within a very short time by feeding back the test results and, therefore, it is possible to control the dye liquor with a high accuracy over a very wide concentration range.

Other objects and characteristics will become clear from the detailed description of the invention mentioned later together with the attached drawings.

DETAILED DESCRIPTION OF THE INVENTION

Figure 1:
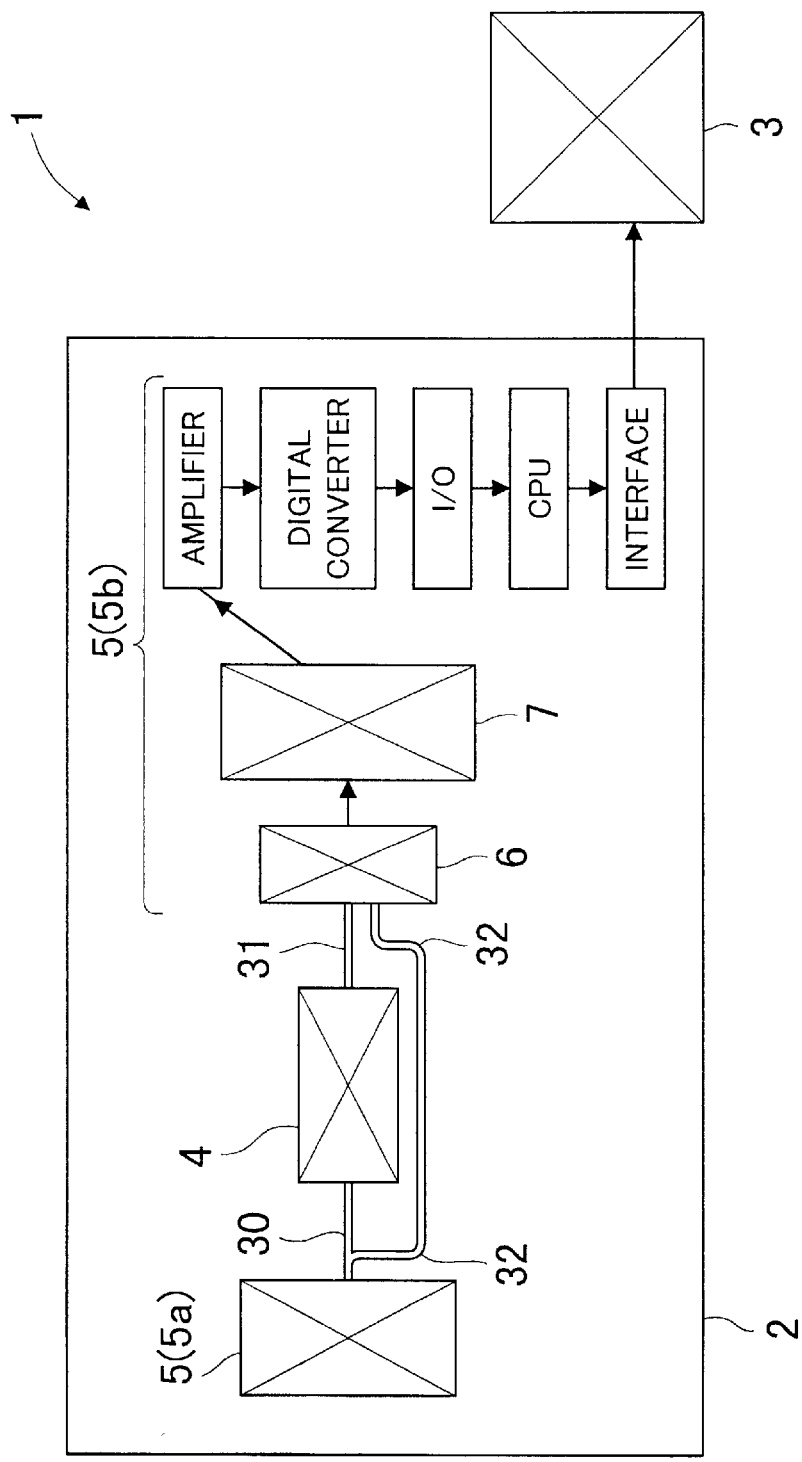
FIG. 1 is a schematic diagram showing a constitution of an automatic color-tone test device in compliance with one embodiment of the invention.

Hereunder, one embodiment of an automatic color-tone test device of the present invention is described while referring to the drawings. In the automatic color-tone test device 1 shown in FIG. 1, 2 is a spectrophotometer, 3 is a statistical test computer section, and the spectrophotometer 2 comprises a measurement cell 4 and a photometer body section 5.

The photometer body section 5 is one publicly known as the body section of the spectrophotometer, and comprises a light source portion 5a such as halogen lamp and a spectral analysis portion 5b for performing mainly a spectral analysis. Outline of a measurement in the spectrometer 2 is as follows. That is, a light projected from the light source portion 5a is projected into the measurement cell 4 through a projection optical fiber 30, the light having passed through the measurement cell 4 is introduced into a double beam attachment 6 by means of being guided by a receiving optical fiber 31 and further separated into its spectral components 7 and, furthermore, an absorbance at each wavelength, i.e. absorption curve (absorbance curve), is measured by publicly known detection means. Incidentally, 32 is a monitoring optical fiber for monitoring a change with the passage of time in intensity of the light from the light source 5a and, on the basis of this, a 0-point compensation in the absorbance measurement is performed, thereby improving a measurement accuracy. Further, as to a type of the spectrometer 2, it is not especially limited, but a photodiode array type is desirable in a point of measuring speed. Further, in case where a dye liquor of measurement object is one generating a scattered light such as colloid aqueous solution and suspension liquor, it is preferable to measure using an integrating sphere and, among others, a totally spherical integrating sphere (integrating sphere having no hole except light-incoming section and light-outcoming section) is especially suitable.

Figure 2:
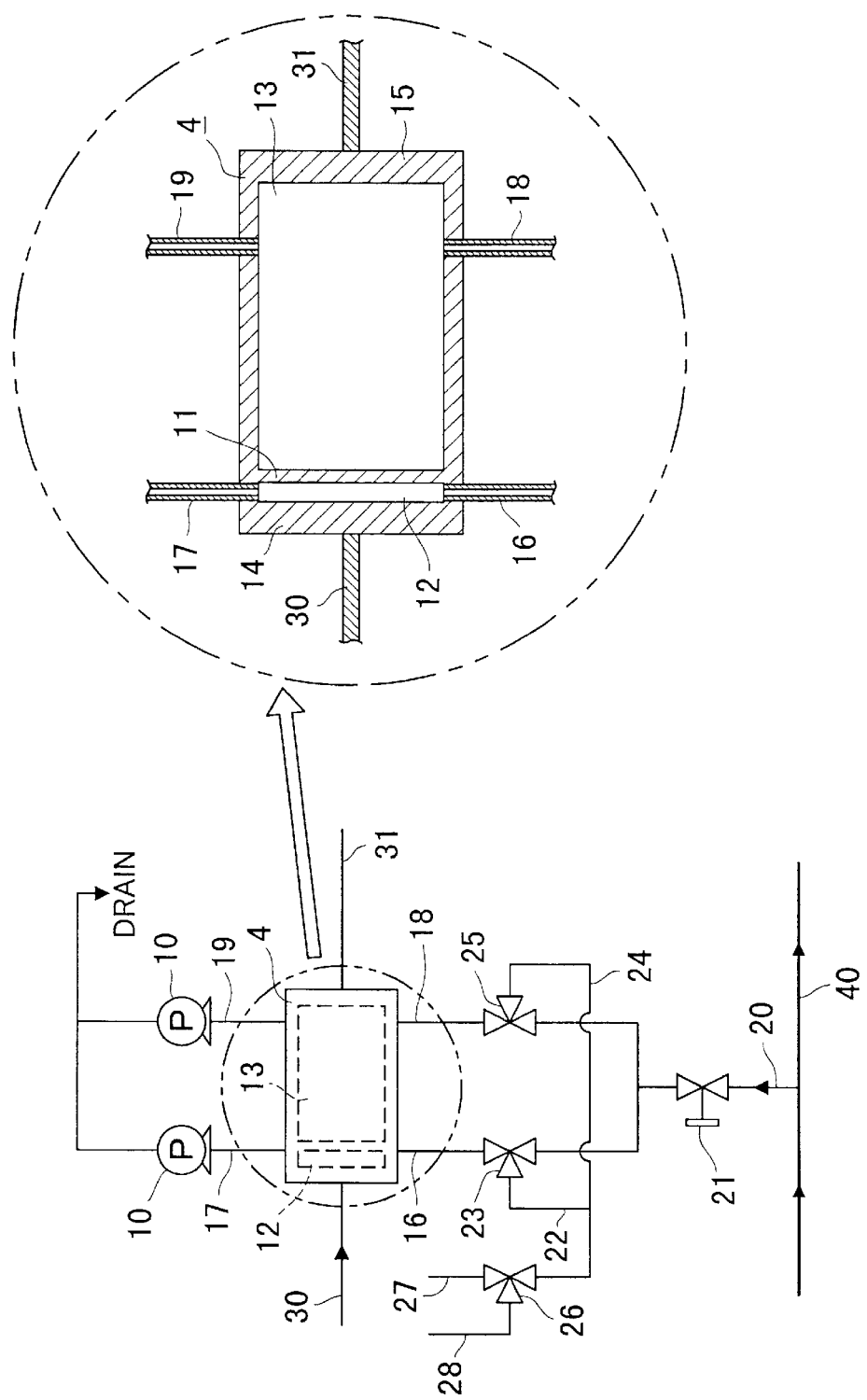
FIG. 2 is a system diagram showing a connection mode of measurement cell, piping and optical passage.

As shown in FIG. 2, the measurement cell 4 is a quartz glass made cell having a rectangular shape in section, and its internal space is divided by a quartz glass made partition plate 11 into two liquid-tight independent spaces mutually different in light transmission distance. That is, it is divided under a liquid-tight state into a first independent space 12 and a second independent space 13. The light transmission distance of the second independent space 13 is set to be considerably larger than that of the first independent space 12, and it is preferable to constitute such that the light transmission distance of the second independent space 13 becomes 10–50 times that of the first independent space 12. Incidentally, "light transmission distance" means a distance through which a measurement light has transmitted the dye liquor itself of a measurement object.

The projection optical fiber 30 is connected to a side wall 14 at one end side in a longitudinal direction of the measurement cell 4. That is, the projection optical fiber 30 is disposed under a state that its projection face at tip butts against the side wall 14. Further, the receiving optical fiber 31 is connected to a side wall 15 at the other end side in a longitudinal direction of the measurement cell 4 similarly under a state that its receiving face at tip butts against the side wall 15. An axis of the projection optical fiber 30 and that of the receiving optical fiber 31 are disposed so as to agree with each other, so that the light projected from the projection optical fiber 30 passes through the first independent space 12 and the second independent space 13 in this order and, thereafter, is introduced into the receiving optical fiber 31 from the receiving face of the receiving optical fiber 31. Incidentally, the projection optical fiber 30 may be disposed so as to be spaced from the side wall 14 of the measurement cell 4 without being butted thereagainst. Also as to the receiving optical fiber 31, the same may be said. Incidentally, although not shown in the drawings, the measurement cell 4 is disposed in a darkroom box capable of shielding an outside light.

To the measurement cell 4, there are connected a first dye liquor introduction tube 16 and a first dye liquor discharge tube 17 such that they are communicated facing each other with the first independent space 12. Further, to the measurement cell 4, there are connected a second dye liquor introduction tube 18 and a second dye liquor discharge tube 19 such that similarly they are communicated facing each other with the second independent space 13.

The first dye liquor discharge tube 17 and the second dye liquor discharge tube 19 are respectively provided with peristaltic pumps 10, 10, and these both discharge tubes 17, 19 join and are connected to a drain (not shown). The peristaltic pump 10 is a pump for keeping a pressure in the measurement cell 4 constant by suppressing the pressure in the tube when it is too high and, on the other hand, sucking a liquor when it is too low.

On the other hand, the first dye liquor introduction tube 16 and the second dye liquor introduction tube 18 are joined, and communication-connected to a dye liquor sampling tube 20. The dye liquor sampling tube 20 is branched and connected to a dye liquor feed tube 40 for feeding the dye liquor controlled by the automatic controlling device to a dyeing machine and the like. The dye liquor sampling tube 20 is provided with a pressure regulation valve 21, and it is so adapted that a dye liquor flow rate sampled from the dye liquor feed tube 40 can be regulated by the pressure regulation valve 21.

Further, at midway of the first dye liquor introduction tube 16 there is branched a first flow tube 22, and at the branched portion there is provided a first switch valve 23. Similarly, at midway of the second liquor introduction tube 17 there is branched a second flow tube 24, and at the branched portion there is provided a second switch valve 25. The other ends of the first flow tube 22 and the second flow tube 24 join and are connected to a third switch valve 26. To the remaining two ends of the third switch valve 26 there are respectively connected a feed tube 27 through which a water is passed and a cleaning water introduction tube 28.

In the automatic color-tone test device 1, the controlling dye liquor is selectively fed into one independent space properly among the first independent space 12 and the second independent space 13, and such a selective operation is performed by a switching of the first switch valve 23 and the second switch valve 25.

Figure 3A:
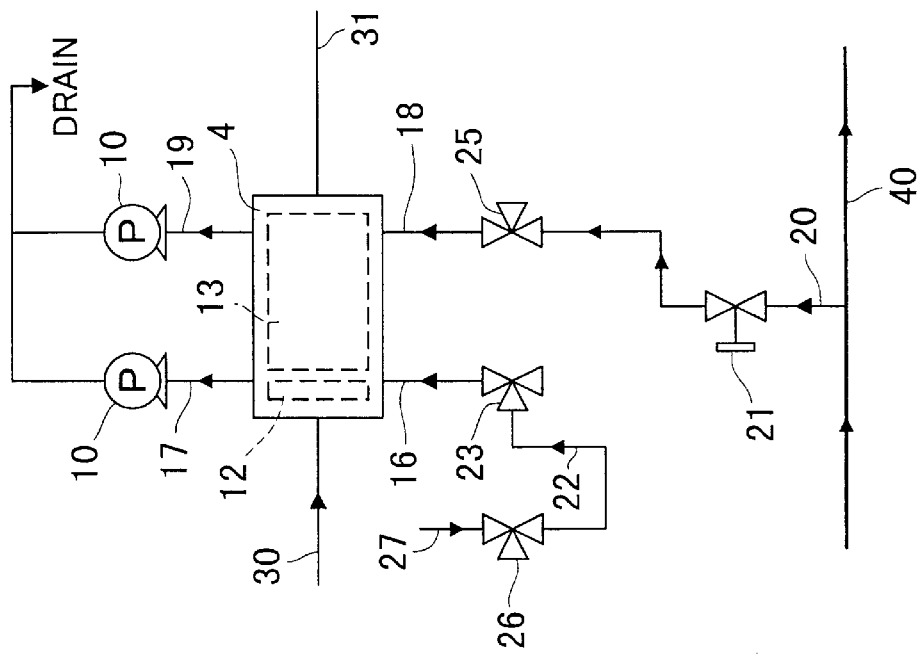
FIG. 3 is an explanatory diagram showing passages of liquor, wherein A shows a case where a concentration of dye liquor is in a high concentration region, and B shows a case where a concentration of dye liquor is in a low concentration region.

That is, in case where a concentration level of the controlling dye liquor, that is a measurement object, is in a high concentration region, as shown in FIG. 3A, by the switching of the first switch valve 23, the dye liquor is fed into the first independent space 12 through the dye liquor sampling tube 20 and the first dye liquor introduction tube 16 from the dye liquor feed tube 40; while, by the switching of the second switch valve 25 and the third switch valve 26, a reference liquid (for example, water) is fed into the second independent space 13 through the feed tube 27, the second flow tube 24 and the second dye liquor introduction tube 18. In this case, a light transmission distance in the measurement cell 4 is a distance over which the light transmits within the first independent space 12 through which the dye liquor is being fed. Since the light transmission distance is set short, it is possible to perform an absorbance measurement without any difficulty within a measurement range ability of the spectrophotometer also in case where the concentration of the controlling dye liquor is high.

Figure 3B:
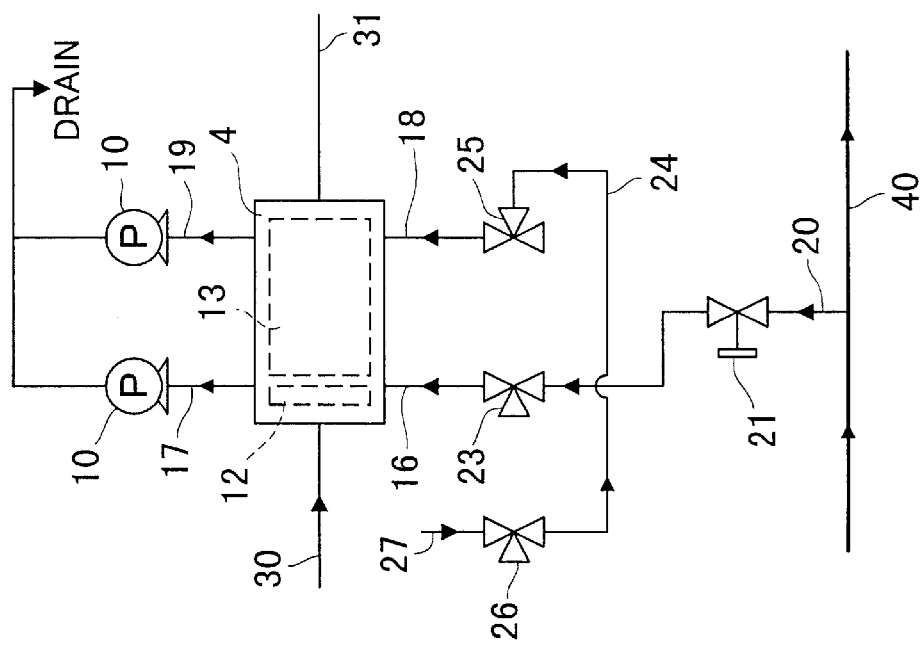

Contrary to this, in case where a concentration level of the controlling dye liquor, that is a measurement object, is in a low concentration region, as shown in FIG. 3B, by the switching of the second switch valve 25, the dye liquor is fed into the second independent space 13 through the dye liquor sampling tube 20 and the second dye liquor introduction tube 18 from the dye liquor feed tube 40; while, by the switching of the first switch valve 23 and the third switch valve 26, a reference liquid (for example, water) is fed into the first independent space 12 through the feed tube 27, the first flow tube 22 and the first dye liquor introduction tube 16. In this case, a light transmission distance in the measurement cell 4 is a distance over which the light transmits within the second independent space 13 through which the dye liquor is being fed. Since the light transmission distance is set long, it is possible to perform an absorbance measurement without any difficulty within a measurement range ability of the spectrophotometer also in case where the concentration of the controlling dye liquor is low.

Incidentally, prior to introducing the dye liquor into the first independent space 12 or the second independent space 13, it is desirable to previously perform the 0-point compensation by introducing the reference liquor into the first independent space 12 and the second independent space 13 and performing a reference measurement under this state.

Furthers on changing the liquor fed into the first independent space 12 or the second independent space 13 (change of a kind of the controlling dye liquor, or change between the controlling dye liquor and the water, and the like), the cleaning water is fed into the first independent space 12 or the second independent space 13 for a fixed time from the cleaning water introduction tube 28 by the switching of the first switch valve 23, the second switch valve 25 or the third switch valve 26 as the occasion demands. In this manner, by feeding the cleaning water into the first independent space 12 or the second independent space 13 for a fixed time, it is possible to precisely exchange the feed liquor within a shorter time expelling a remaining liquor. As such a cleaning water, there are enumerated, although not especially limited, a cleaning water and the like having a relatively high polarity such as water/dimethylformamide mixed liquor and water/isopropyl alcohol mixed liquor, for instance.

On the other hand, the statistical test computer section 3 is a device for operation-judging whether or not the dye liquor's concentration and hue measured by the spectrophotometer 2 concerning the above constitution agree with desired values.

And, when the dye liquor controlled by the automatic controlling device is tested in its color-tone by using the automatic color-tone test device 1 having the above constitution, firstly data of the dye liquor's desired concentration and hue, i.e. data of the absorbance curve, is caused to be preliminarily recognized in the statistical test computer section 3. Then, it is judged whether a concentration level of the dye liquor controlled by the automatic controlling device is in the high concentration region or in the low concentration region. In case of the former, switching of the first, second and third switch valves 23, 25 and 26 is performed such that the dye liquor is selectively fed into the first independent space 12, i.e. such that the above-mentioned passage shown in FIG. 3A is formed. On the other hand, in case of the latter, switching of the first, second and third switch valves 23, 25 and 26 is performed such that the dye liquor is selectively fed into the second independent space 13, i.e. such that the above-mentioned passage shown in FIG. 3B is formed. Such a switching of the switch may be manually performed, or may be automatically performed by a valve control device and the like.

According to the automatic color-tone test device 1 of the invention, in case where a concentration level of the controlling dye liquor, that is a measurement object, is in a high concentration region, since it is possible to selectively introduce the controlling dye liquor into the first independent space 12 in which the light transmission distance is set small, it is possible to perform an absorbance measurement without any difficulty within a measurement range ability of the spectrophotometer. On the other hand, in case where a concentration level of the controlling dye liquor, that is a measurement object, is in a low concentration region, since it is possible to selectively introduce the controlling dye liquor into the second independent space 13 in which the light transmission distance is set large, it is possible to perform an absorbance measurement without any difficulty within a measurement range ability of the spectrophotometer. Therefore, the color-tone test can be performed within a very short time even for the dye liquor of any concentration over a very wide concentration range from a low concentration to a high concentration. Further, in any of the above case, since the absorbance measurement is performed under a state that the dye liquor is being fed in the first independent space 12 or the second independent space 13, there is an advantage that the color-tone test of the dye liquor being fed after being continuously controlled by the automatic controlling device can be performed almost momentarily and continuously. Accordingly, a flow rate adjustment can be performed by momentarily and continuously feeding back the color-tone test results to the automatic controlling device, and an automatic control of the dye liquor can be performed very precisely.

Figure 4:
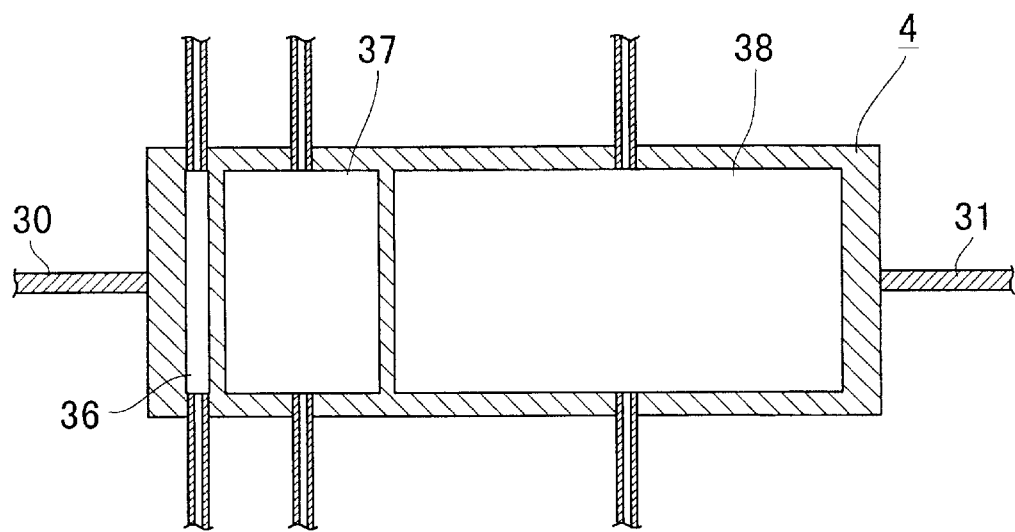
FIG. 4 is a sectional view showing a modified example of a constitution of the measurement cell.

Incidentally, in the above embodiment, there is adopted a constitution in which an internal space of the measurement cell 4 is divided into two liquid-tight independent spaces 12, 13 mutually different in light transmission distance, but it is not limited to such a constitution, and as shown in FIG. 4 there may be adopted a constitution in which it is divided into three liquid-tight independent spaces 36, 37, 38 for instance. If such a constitution in which it is divided into three liquid-tight independent spaces is adopted, it is possible to perform the color-tone test within a very short time for the dye liquor of any concentration over a wider concentration range. Of course, there may be adopted a constitution in which it is divided into four or more plural liquid-tight independent spaces.

As mentioned above, the automatic color-tone test device of the invention can perform the color-tone test within a very short time even for the dye liquor of any concentration over a very wide concentration range from a low concentration to a high concentration and can feed back the test results so to speak continuously within a very short time, so that it is suitable as a color-tone test device in an automatic controlling system for dye liquor, for instance.

Figure 5:
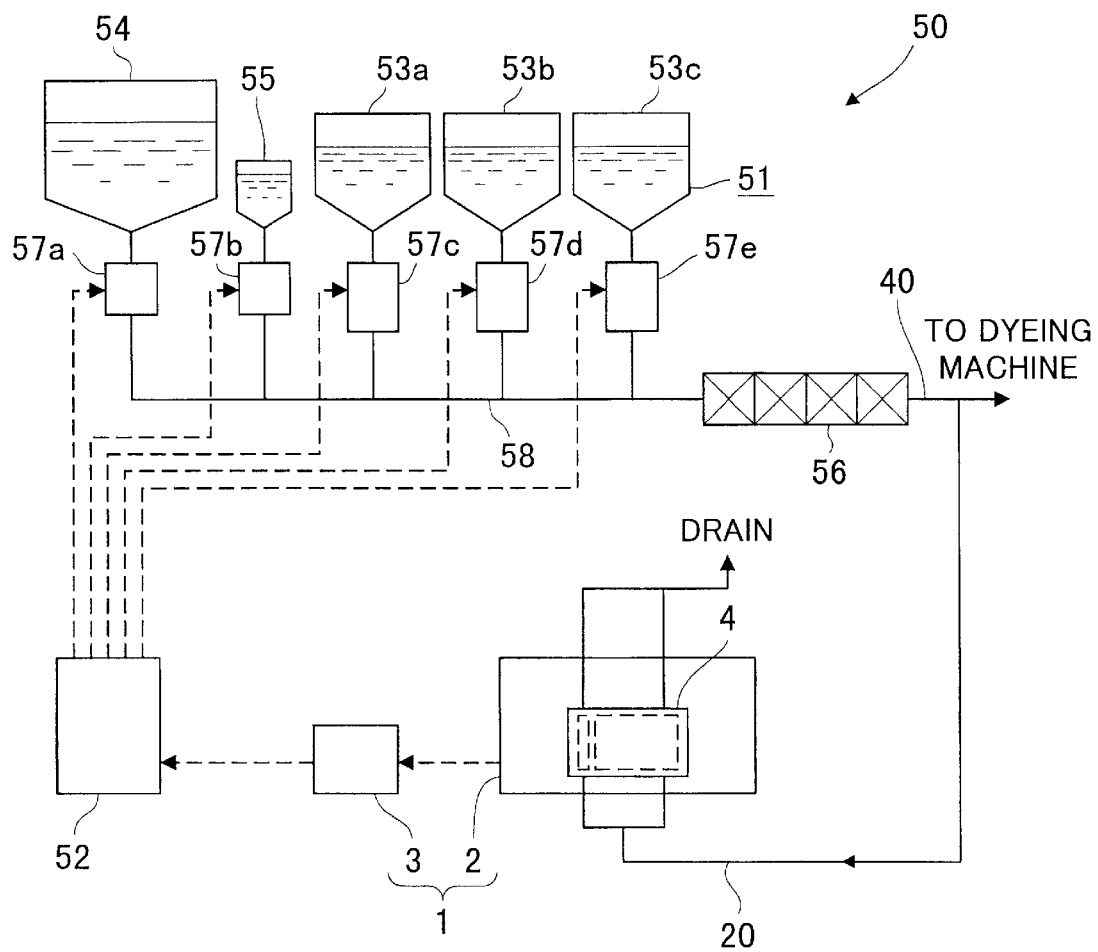
FIG. 5 is a schematic diagram showing a constitution of an automatic controlling system for dye liquor in compliance with one embodiment of the invention.

FIG. 5 shows one embodiment of an automatic controlling system having the automatic color-tone test device 1 of the invention. The automatic controlling system 50 comprises the automatic color-tone test device 1 of the above constitution, an automatic controlling device 51 and a control computer section 52.

The automatic controlling device 51 comprises dye mother liquor tanks 53a, 53b, 53c filled with a mother liquor, a water tank 54 filled with a water, an assistant tank 55 filled with assistants, a mixer 56 for mixing the liquors fed from each tank, and flow rate control devices 57a, 57b, 57c, 57d, 57e for controlling a feed flow rate from each tank to the mixer.

Figure 6:
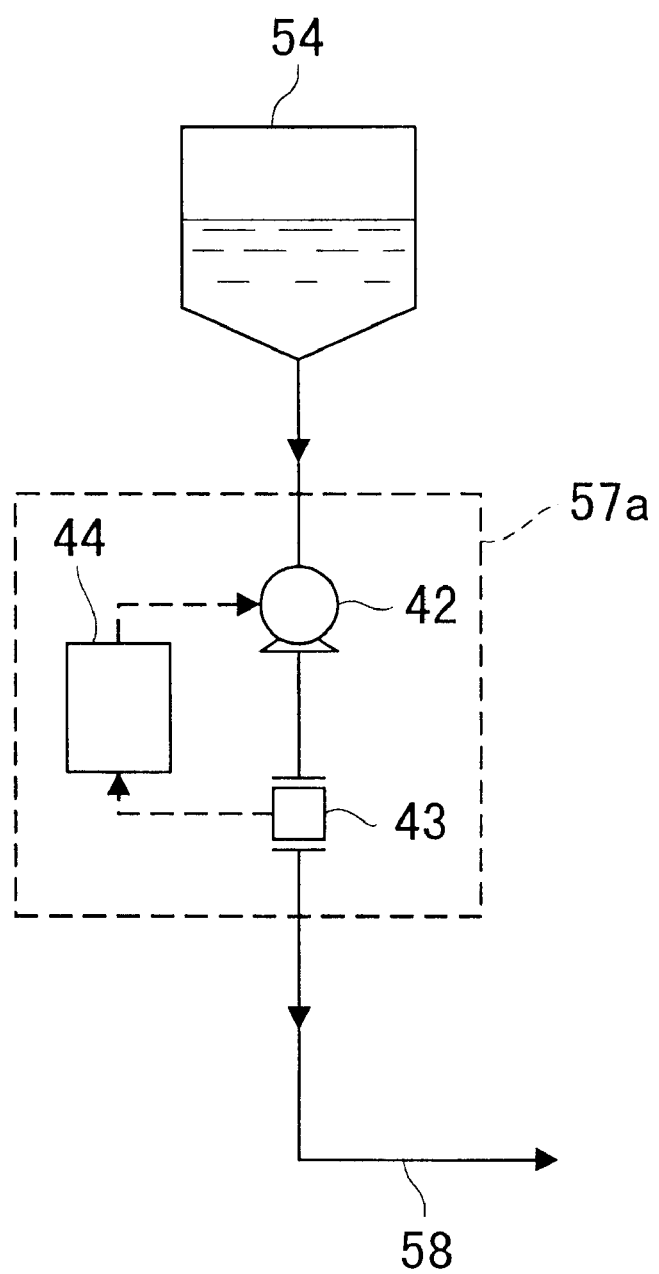
FIG. 6 is a system diagram showing a constitution of a flow rate control device of water tank and assistant tank.

The flow rate control device 57a for controlling a flow rate of water fed from the water tank 54 is caused to control a flow rate of the water fed from the water tank 54 by cooperating with a pump 42, a flow rate meter 43 and a control device 44 as shown in FIG. 6. Further, also a constitution of the flow rate control device 57b for controlling a flow rate of assistants fed from the assistant tank 55 is similar to this.

Figure 7:
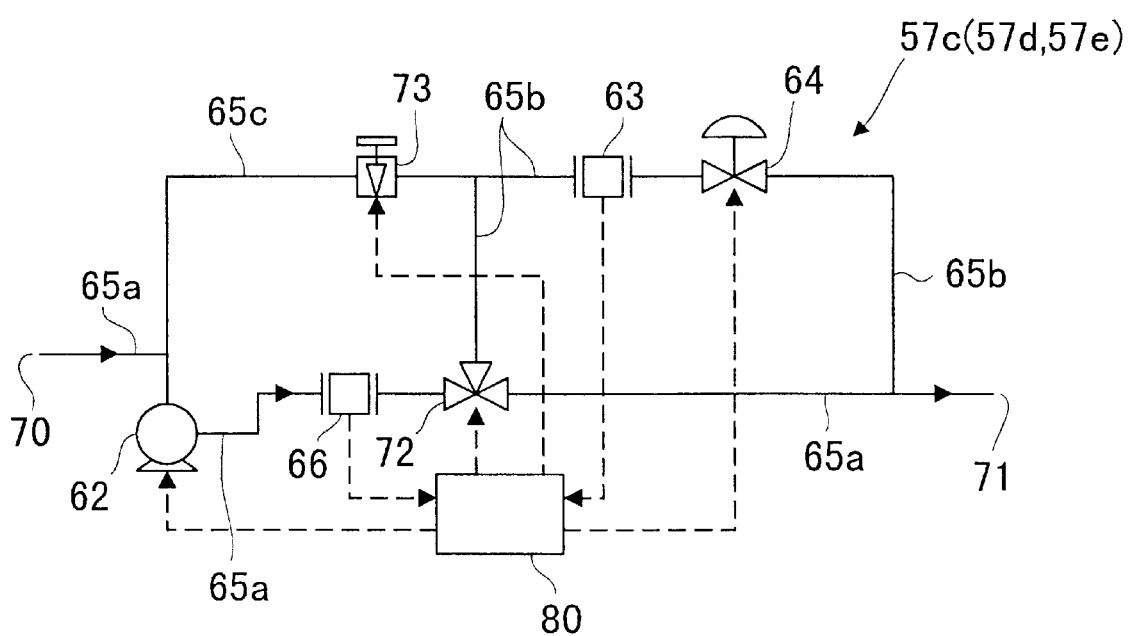
FIG. 7 is a system diagram showing a constitution of a flow rate control device of dye mother liquor tank.
Figure 8A:
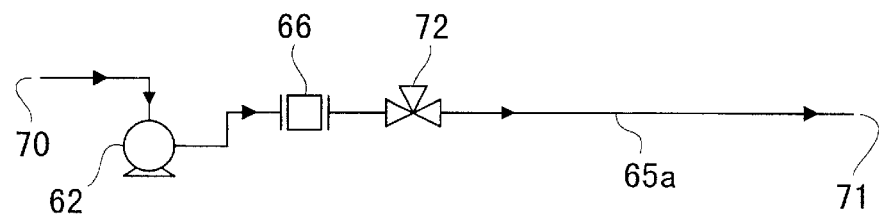
FIG. 8 is a diagram showing passages of the dye liquor in the flow rate control device of FIG. 7, wherein A shows a case where the dye liquor is fed in large flow rate, and B shows a case where the dye liquor is fed in small flow rate.
Figure 8B:
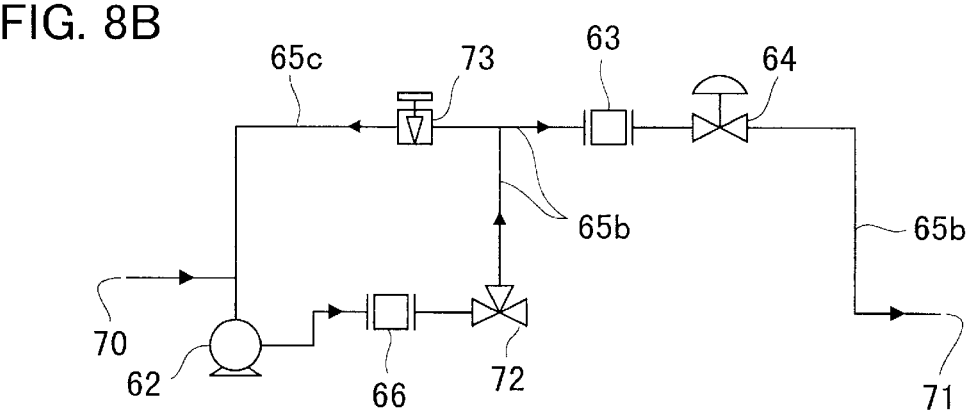

On the other hand, the flow rate control devices 57c, 57d, 57e for controlling a flow rate of each dye liquor fed from the dye mother liquor tanks 53a, 53b, 53c are flow rate control devices capable of variably controlling the flow rate of the dye liquor from the dye mother liquor tank over a wide flow rate range from a small flow rate to a large flow rate in order to make it possible to control with a high accuracy the dye liquor over a very wide range from a low concentration to a high concentration. FIG. 7 is a system diagram showing the constitution thereof, FIG. 8A is an explanatory view showing a passage in case where the dye liquor is fed in large flow rate, and FIG. 8B is an explanatory view showing a passage in case where the dye liquor is fed in small flow rate.

In these drawings, 62 is a pump, 63 a bypass conduit flow meter, 64 a regulation valve, 65 a conduit, and the conduit 65 is constituted by a main conduit 65a, a bypass conduit 65b and a return conduit 65c.

The main conduit 65a has at its one end a suction port 70 for taking in the dye liquor from the dye mother liquor tank and at its the other end a discharge port 71 for the dye liquor. The pump 62 is provided at a position of a side of the suction port 70 of the main conduit 65a. As the pump 62, there is suitably used a positive displacement pump, among others a gear pump, from a viewpoint that it has a large discharge ratio and is excellent in its accuracy.

Further, the main conduit 65a is provided with a main conduit flow meter 66 at a position of more discharge port 71 side than the pump 62. As the flow meter 66, there is suitably used an electromagnetic flow meter from a viewpoint that it has a large range ability and is excellent in its accuracy. A flow rate measured value detected by the flow meter 66 is transmitted to a control device 80, and an adjustment of discharge amount from the pump 62 is performed by the control device 80 on the basis of the measured value. Incidentally, the main conduit flow meter 66 is not necessarily needed to be provided, but it is desirable to be provided from a viewpoint of increasing an accuracy of the flow rate control.

Furthermore, the bypass conduit 65b is branched from a position of more discharge port 71 side than the main conduit flow meter 66 in the main conduit 65a and the branched portion is provided with a switch valve 72, while the other end of the bypass conduit 65b is joined with the main conduit 65a before reaching the discharge port 71. By switching the switch valve 72, it is selected whether the dye liquor passing through the pump 62, flowing through the main conduit 65a and reaching the branched portion is fed through the main conduit 65a as it is or fed to the bypass conduit 65b. This switching control of the switch valve 72 is performed by the control device 80.

The bypass conduit 65b is provided with a bypass conduit flow meter 63 and a regulation valve 64.

As the bypass conduit flow meter 63, there is suitably used an electromagnetic flow meter from a viewpoint that it has a large range ability and is excellent in its accuracy. And, a flow rate measured amount detected by the flow meter 63 is transmitted to the control device 80, and an opening adjustment of the regulation valve 64 is performed by the control device 80 on the basis of the measured value.

Figure 9A:
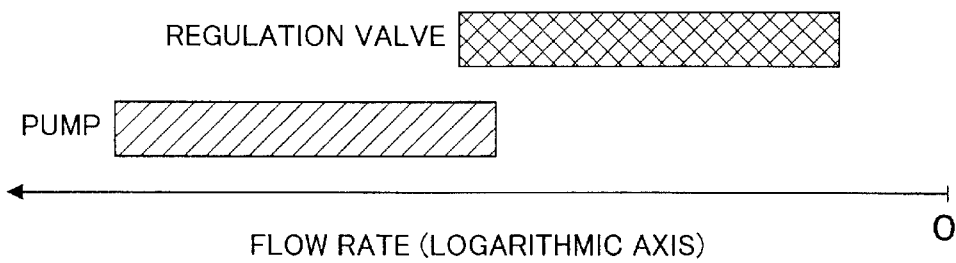
FIG. 9 is an explanatory diagram showing an example of correlation between a discharge flow rate range of pump and a regulation valve.
Figure 9B:
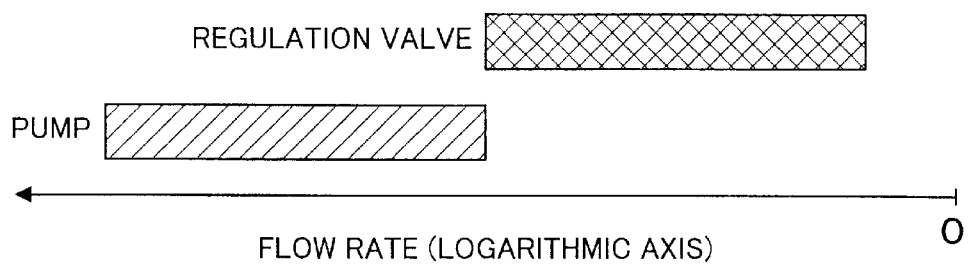
Figure 9B:
Figure 9B:

As the regulation valve 64, there is used one which can control a flow rate range in a lower flow rate range than a discharge flow rate range capable of being controlled at least by the pump 62. At this time, it is preferable that a lower limit region of the discharge flow rate range capable of being controlled by the pump 62 and an upper limit region of the flow rate range capable of being controlled by the regulation valve 64 are set such that they are partly overlapped as shown in FIG. 9A, or a lower limit value capable of being controlled by the pump 62 and an upper limit value capable of being controlled by the regulation valve 64 are set such that they substantially agree with each other as shown in FIG. 5B. By setting in this manner, since a non-controllable region does not exist between the flow rate range capable of being controlled by the pump 62 and the flow rate range capable of being controlled by the regulation valve 64, it becomes possible to variably control the flow rate with a high accuracy over a wide flow rate range from a small flow rate to a large flow rate without allowing the non-controllable region to exist. Of course, the regions where the flow rate ranges capable of being controlled respectively by the pump 62 and the regulation valve 64 overlap may be made larger than the overlapping range shown in FIG. 9A, but in this case it follows that the flow rate range where the variable control with a high accuracy becomes possible is more reduced than the former.

Further, the return conduit 65c is provided in such a manner that a position of more suction port 70 side than the flow meter 63 in the bypass conduit 65b is communication-connected with a position of more suction port 70 side than the pump 62 in the main conduit 65a. The return conduit 65c is provided in order to effectively utilize the dye liquor without wasting it by joining the dye liquor becoming excess owing to the fact that, in case where the dye liquor is caused to flow through the bypass conduit 65b, a flow rate control is performed by the regulation valve 64 with the dye liquor fed from the suction port 70 at a position of more suction port 70 side than a pump 62 setting position of the main conduit 65a, thereby returning it to the main conduit 65a again.

The return conduit 65c is provided with a needle valve 73 for opening/closing the passage of the return conduit 65c. The needle valve 73 is opened/closed by the control device 80 and, in case where the dye liquor is passed only through the main conduit 65a, the needle valve 73 is closed in order that the dye liquor does not flow back into the return conduit 65c.

The control computer section 52 performs a multicomponent analysis on the basis of operation judgment results in the statistical test computer section 3, and is adapted such that command signals of flow rate adjustment are transmitted as occasion demands to each control device 44, 44, 80, 80, 80 of each flow rate control device 57a, 57b, 57c, 57d, 57e on the basis of results of the multicomponent analysis. Incidentally, in this embodiment, there is adopted a constitution in which each control device 44, 44, 80, 80, 80 is individually provided for every each flow rate control device, but it is also possible to adopt a constitution in which one control device for controlling together, for example, all of these flow rate control devices 57a, 57b, 57c, 57d, 57e is provided.

And, when the dye liquor is controlled using the automatic controlling system 50, firstly data of the dye liquor's desired concentration and hue, i.e. data of the absorbance curve, is caused to be preliminarily recognized in the statistical test computer section 3. The control computer section 52 reads the data (absorbance curve) and, by the multicomponent analysis, commands with how much flow rate each liquor should be fed from each dye mother liquor tank 53a, 53b, 53c, the water tank 54 and the assistant tank 55 for every each flow rate control device 57a, 57b, 57c, 57d, 57e. That is, it is commanded to each control device 44, 44, 80, 80, 80.

By the command of the control computer section 52, the dye liquor, the water and the assistant in a predetermined flow rate are respectively fed to a feed tube 58 from each dye mother liquor tank 53a, 53b, 53c, the water tank 54 and the assistant tank 55, and these are sufficiently evenly mixed by the mixer 56 and become a controlling dye liquor, and the controlling dye liquor is fed to a feed tank of a dyeing machine and the like through a dye liquor feed tube 40.

Control of a dye liquor flow rate in each dye mother liquor tank 53a, 53b, 53c is performed as follows. By the control computer section 52, a set flow rate value or a flow rate setting program for every each dye mother liquor tank 53a, 53b, 53 c is commanded to each control device 80, 80, 80 of the flow rate control devices 57c, 57d, 57e, and on receiving this each control device 80 judges whether the set flow rate value is in a large flow rate range within which the flow rate can be controlled only by the pup 62 or in a small flow rate range within which the flow rate can be controlled by a cooperation of the pump 62 and the regulation valve 64. In case of the former the main switch valve 72 is switched so as to be communicated with the main conduit 65a, while in case of the latter the main switch valve 72 is switched so as to be communicated with the bypass conduit 65b.

FIG. 8A is a diagram showing a passage in case where the dye liquor is fed in a large flow rate. As mentioned before, by the control device 80, the main switch valve 72 is switch-controlled so as to communicate with the main conduit 65a, while the needle valve 73 provided in the return conduit 65c is closed. Accordingly, the dye liquor sucked from the suction port 10 by a drive of the pump 62 passes through only the main conduit 65a as shown in FIG. 8A, and discharged from a discharge port 71 and fed to the feed tube 58. In this time, since it is adapted such that the flow rate fed by the pump 62 is successively monitored by the main conduit flow meter 66 and, in case where the monitored flow rate value deviates from a desired flow rate value, since an opening adjustment of the pump 62 is performed by signals from the control device 80, it is possible to feed the dye liquor in a large flow rate while performing a flow rate control always with a high accuracy.

On the other hand, FIG. 8B is a diagram showing a passage in case where the dye liquor is fed in a small flow rate. By the control device 80, the main switch valve 72 is switch-controlled so as to communicate with the bypass conduit 65b, while the needle valve 73 provided in the return conduit 65c is set to an opened state (opening is about 50%). And by the control device 80, as to the pump 62 an opening adjustment is performed such that a minimum flow rate or a low flow rate is achieved within a range of capable of being controlled with a high accuracy, while as to the regulation valve 64 an opening adjustment is performed on the basis of a correlation with an opening of the pump 62 such that a discharged flow rate becomes a desire flow rate. Accordingly, as shown in FIG. 8B, the dye liquor sucked from the suction port 70 by a drive of the pump 62 passes through the main conduit 65a and reaches the main switch valve 72, and from here flows into the main conduit 65a and, after being controlled in its flow rate by the regulation valve 64, further passes through the bypass conduit 65b and is discharged from the discharge port 71 and is fed to the feed tube 58. In this time, since it is adapted such that the flow rate fed through the bypass conduit 65b is successively monitored by the bypass conduit flow meter 63 and, in case where the monitored flow rate value deviates from a desired flow rate value, since an opening adjustment of the regulation valve 64 is performed by signals from the control device 80, it is possible to feed the dye liquor in a small flow rate while performing a flow rate control always with a high accuracy.

Incidentally, the dye liquor becoming excess by throttling the regulation valve 64 passes through the return conduit 65c and joins with the dye liquor fed from the suction port 70 at a position of more suction port 70 side than a pump 62 setting position in the main conduit 65a. By providing such return conduit 65c, it becomes possible to return the dye liquor having become excess to the main conduit 65a again without wasting it, so that it is economical.

If the flow rate of the dye liquor is controlled by the flow rate control devices 57c, 57d, 57e, in case of feeding the dye liquor in a large flow rate, by making only the main conduit 65a into the passage and adjusting the opening of only the pump 62, it is possible to feed the dye liquor to the feed tube 58 in a large flow rate while controlling the flow rate with a high accuracy within a discharge flow rate range which is inherently controllable by the pump 62. On the other hand, in case of feeding the dye liquor in a small flow rate, the dye liquor fed while being once controlled to a small flow rate by the pump 62 is fed to the bypass conduit 65b and discharged by means of being controlled so as to further throttle it by further adjusting the opening of the regulation valve 64 in the bypass conduit 65b, so that it is possible to feed the dye liquor in a low flow rate far exceeding a lower limit region of the discharge flow rate range which is inherently controllable by the pump 62. In this manner, it is possible to control the flow rate with a high accuracy from a high flow rate corresponding to an upper limit region of the controllable discharge flow rate range possessed by the pump 62 itself to a low flow rate corresponding to a lower limit region of the controllable discharge flow rate range of the regulation valve 64.

In this manner, since the flow rate control devices 57c, 57d, 57e can variably control the flow rate with a high accuracy over a wide flow rate range from a small flow rate to a large flow rate, in the automatic controlling system 50, it is possible to control the dye liquor with a high accuracy from a low concentration to a high concentration over a very wide concentration range.

And, the controlling dye liquor sufficiently evenly mixed by the mixer 56 is fed to the dye liquor feed tube 40 and fed to a feed tank of a dyeing machine and the like. On the other hand, a part of the controlling dye liquor is introduced into the measurement cell 4 from the dye liquor sampling tube 20 branched from the dye liquor feed tube 40, and here the absorbance measurement of the controlling dye liquor that is a measurement object is performed by the spectrophotometer 2 by the above-mentioned method.

Next, the absorbance curve data measured by the spectrophotometer 2 is sent to the statistical test computer section 3. In the statistical test computer section 3, an operation judgment as to whether or not the actually measured controlling dye liquor's concentration and hue agree with the previously inputted data of the desired dye liquor's concentration and hue is performed.

On the basis of the operation judgment results in the statistical test computer section 3, the multicomponent analysis is performed in the control computer section 52 and, on the basis of the multicomponent analysis results, a command signal of the flow rate adjustment is transmitted for every each flow rate control device 57a, 57b, 57c, 57d, 57e as occasion demands.

In the automatic controlling device 50, since a time required from the sampling of the dye liquor to reaching the absorbance measurement in the spectrophotometer 2, the judgment in the statistical test computer section 3, and the multicomponent analysis and the flow rate adjustment command in the control computer section 52 is in the order of several seconds, i.e. since the adjustment of flow rate can be performed within a very short time by feeding back the test results, it is possible to control the dye liquor with a high accuracy over a very wide concentration range.

Further, since a time required to feed back the test results is very short, if it is set to perform the absorbance measurement of the controlling dye liquor at an interval of every 1–10 seconds for instance, the flow rate adjustment can be performed by momentarily and continuously feeding back the color-tone test results to the automatic controlling device 51, so that it is possible to automatically control the dye liquor with a very high accuracy.

In the above embodiment, there is adopted a constitution in which the three dye mother liquor tanks are provided, but of course the number of the dye mother liquor tanks is not especially limited, and it may be one or several. Further, the assistant tank may be provided as occasion demands, and there is no limitation on the number thereof.

Figure 10:
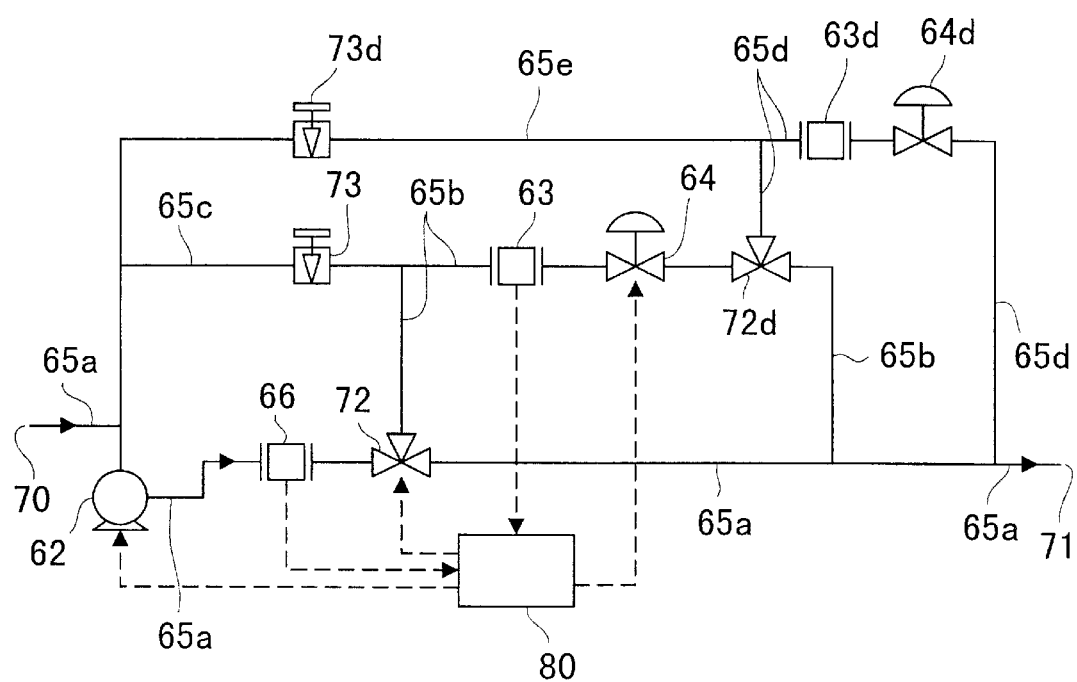
FIG. 10 is a system diagram showing a modified example of the flow rate control device of the dye mother liquor.

Incidentally, in the flow rate control device 57c, 57d, 57e, the bypass conduit 65b may be further provided with a second bypass conduit 65d. That is, as shown in FIG. 10 for instance, the second bypass conduit 65d is branched from a position of more discharge port side than positions where the bypass conduit flow meter 63 and the regulation valve 64 are provided in the bypass conduit 65b through a sub-switch valve 72d. The second bypass conduit 65d is provided with a second bypass conduit flow meter 63d and a second bypass conduit regulation valve 64d. The other end of the second bypass conduit 65d is joined with the main conduit 65a before the discharge port 71, and a second return tube 65e having a second needle valve 73d is provided in such a manner that a position of more suction port 70 side than the second bypass conduit flow meter 63d in the second bypass conduit 65d is communication-connected to the return conduit 65c. Since the bypass conduit is constituted in two stages in this manner, i.e. since it becomes possible to feed the dye liquor controlled to a low flow rate by the bypass conduit 65b and to throttle it to a further low flow rate by the second bypass conduit regulation valve 64d of the second bypass conduit 65d, it becomes possible to variably control the flow rate with a high accuracy over a wider flow rate range than the one in which the bypass conduit is constituted in one stage.

Of course, for the second bypass conduit, a third bypass conduit may be further provided in a manner similar to the above. By this, it is possible to variably control the flow rate with a high accuracy over a wider flow rate range.

Next, a concrete embodiment of the invention is described.

Embodiment 1

By means of using the automatic controlling system 50 having the above-mentioned constitution shown in FIG. 5, an automatic controlling of the dye liquor was performed by mixing three kinds of dye mother liquors, a water and an assistant, and concentration data of the controlling dye liquor measured by the statistical test computer section 3 was monitored by a personal computer at an interval of every unit time (5 seconds) and was recorded. And, an error from a desired dye liquor adjustment concentration (set concentration) is found, and therefrom an error ratio {[(actual measurement value−set value)÷set concentration]× 100} is found per a unit time, and a mean value of the error ratio was found. The results in case where the controlling dye liquor concentration is in a low concentration region (0.001–0.05 g/L) are shown in Table 1, those in case where it is in a high concentration region (0.05–0.5 g/L) are shown in Table 2, and those in case where a blending of the three kinds of dye mother liquors is an unequal blending are shown in Table 3.

Incidentally, as the spectrophotometer, a spectrophotometer (MCPD-3000) made by Ohtsuka Denshi was used, and a measurement wavelength range when the absorbance measurement was performed using this was set to 400–700 nm.

Further, as the three kinds of the dyes, there were used Lanasyn Yellow S-2GL (trade name: made by Sando Co., Ltd.), Lanasyn Black BRL (trade name: made by Sando Co., Ltd.) and Lanasyn Red SG (trade name: made by Sando Co., Ltd.), and each dye mother liquor concentration was set to 10 g/L.

TABLE 1

| Controlling Dye Liquor No | Lanasyn Yellow S-2GL | | Lanasyn Black BRL | | Lanasyn Red SG | |
|---|---|---|---|---|---|---|
| | Set Concentration (g/L) | Error Ratio (%) | Set Concentration (g/L) | Error Ratio (%) | Set Concentration (g/L) | Error Ratio (%) |
| 1 | 0.005 | −0.34 | 0.005 | −0.07 | 0.005 | 0.01 |
| 2 | 0.010 | 1.05 | 0.010 | −0.13 | 0.010 | 0.19 |
| 3 | 0.015 | 0.20 | 0.015 | 0.18 | 0.015 | −0.09 |
| 4 | 0.020 | 0.08 | 0.020 | −0.24 | 0.020 | −0.15 |
| 5 | 0.025 | 0.25 | 0.025 | 0.01 | 0.025 | 0.07 |
| 6 | 0.030 | −0.09 | 0.030 | 0.05 | 0.030 | 0.02 |
| 7 | 0.035 | −0.01 | 0.035 | −0.02 | 0.035 | −0.02 |
| 8 | 0.040 | −0.34 | 0.040 | 0.03 | 0.040 | 0.11 |
| 9 | 0.045 | −0.16 | 0.045 | 0.02 | 0.045 | −0.11 |
| 10 | 0.050 | 0.25 | 0.050 | −0.03 | 0.050 | 0.03 |

TABLE 2

| Controlling Dye Liquor No | Lanasyn Yellow S-2GL | | Lanasyn Black BRL | | Lanasyn Red SG | |
|---|---|---|---|---|---|---|
| | Set Concentration (g/L) | Error Ratio (%) | Set Concentration (g/L) | Error Ratio (%) | Set Concentration (g/L) | Error Ratio (%) |
| 11 | 0.10 | −0.15 | 0.10 | 0.03 | 0.10 | 0.01 |
| 12 | 0.15 | 0.26 | 0.15 | 0.07 | 0.15 | −0.02 |
| 13 | 0.20 | 0.05 | 0.20 | 0.01 | 0.20 | 0.05 |
| 14 | 0.25 | −0.14 | 0.25 | −0.24 | 0.25 | −0.13 |
| 15 | 0.30 | −0.22 | 0.30 | 0.35 | 0.30 | 0.05 |

TABLE 2-continued

| Controlling Dye Liquor No | Lanasyn Yellow S-2GL | | Lanasyn Black BRL | | Lanasyn Red SG | |
|---|---|---|---|---|---|---|
| | Set Concentration (g/L) | Error Ratio (%) | Set Concentration (g/L) | Error Ratio (%) | Set Concentration (g/L) | Error Ratio (%) |
| 16 | 0.35 | −0.05 | 0.35 | −0.03 | 0.35 | −0.2 |
| 17 | 0.40 | 0.09 | 0.40 | 0.07 | 0.40 | 0.11 |
| 18 | 0.45 | −0.01 | 0.45 | 0.05 | 0.45 | −0.13 |
| 19 | 0.50 | 0.03 | 0.50 | −0.02 | 0.50 | 0.04 |

TABLE 3

| Controlling Dye Liquor No | Lanasyn Yellow S-2GL | | Lanasyn Black BRL | | Lanasyn Red SG | |
|---|---|---|---|---|---|---|
| | Set Concentration (g/L) | Error Ratio (%) | Set Concentration (g/L) | Error Ratio (%) | Set Concentration (g/L) | Error Ratio (%) |
| 20 | 0.0900 | −0.01 | 0.0270 | 0.01 | 0.0102 | 0.00 |
| 21 | 0.0750 | 0.29 | 0.0225 | −0.09 | 0.0085 | 0.56 |
| 22 | 0.0600 | 0.03 | 0.0180 | 0.04 | 0.0068 | 0.09 |
| 23 | 0.0450 | −0.02 | 0.0135 | −0.05 | 0.0051 | −0.28 |
| 24 | 0.0300 | −0.04 | 0.0090 | 0.20 | 0.0034 | 0.27 |
| 25 | 0.0150 | 0.05 | 0.0045 | 0.01 | 0.0017 | −0.21 |

As may be apparent from Tables 1–3, according to the automatic controlling system of the embodiment 1, even if the controlling dye liquor concentration of the measurement object is in any of the low concentration region and the high concentration region, one color-tone test can be performed within a very short time (in the order of 5 seconds), the test results can be momentarily fed back and, moreover, the flow rate adjustment can be suitably performed by feeding back the test results so to speak continuously (for example, for every unit time of 1–10 seconds), so that it is possible to perform the controlling of the dye liquor with a very high accuracy over a very wide concentration range.

As mentioned above, since the automatic color-tone test device of the invention is adapted such that the light transmission distance in the measurement cell of the spectrophotometer can be variably set in compliance with the concentration level of the controlling dye liquor that is a measurement object, it is possible to adjust the light transmission distance such that it falls in the measurement range ability, so that the color-tone test can be performed within a very short time even for the dye liquor of any concentration over a very wide concentration range from a low concentration to a high concentration.

In case where an internal space of the measurement cell is divided into plural liquid-tight independent spaces mutually different in light transmission distance, where the liquor introduction tube and the dye liquor discharge tube are respectively communication-connected to each liquid-tight independent space, and where it is so adapted that the controlling dye liquor is selectively fed into any one of the independent spaces in compliance with a concentration level of the controlling dye liquor that is a measurement object, since the light transmission distance in each independent space through which the controlling dye liquor is caused to pass is non-variable and fixed, it is possible to maintain the light transmission distance at a time of measurement to a high accuracy.

Since the automatic controlling system for dye liquor is one for performing the color-tone test by using the above automatic color-tone test device, it is possible to perform the color-tone test within a very short time for the dye liquor of any concentration over a very wide concentration range from a low concentration to a high concentration and, therefore, it is possible to perform an adjustment of the dye liquor with a high accuracy by continuously feeding back the test results within a very short time, so that it is possible to control the dye liquor with a high accuracy over the very wide concentration range.

The present application claims a priority on the basis of Japanese Patent Application No. 11-313487, so that its disclosure content constitutes a part of the present application as it is.

Terms and expressions used here are ones used for explanations and not limited to these, so that it should be interpreted that ones equivalent to the features disclosed and described herein are not expelled and various design modifications within a scope of the claimed invention are allowable.

What is claimed is:

1. An automatic color-tone test device comprising:
   a spectrophotometer in which a dye liquor introduction tube for introducing a controlling dye liquor, that is a measurement object, into a measurement cell is communication-connected to the measurement cell, while a dye liquor discharge tube for discharging the dye liquor after having passed through the measurement cell is communication-connected to the measurement such that a light transmission distance in the measurement cell can be variably set in compliance with a concentration level of the controlling dye liquor that is a measurement object; and
   a statistical test computer section for operation-judging whether or not the dye liquor's concentration and hue measured by the spectrophotometer agree with desired values;
   wherein an internal space of the measurement cell is divided into plural liquid-tight independent spaces mutually different in light transmission distance, and the dye liquor introduction tube and dye liquor discharge tube are respectively communication-connected to each liquid-tight independent space so that the controlling dye liquor is selectively fed to any one of the independent spaces in compliance with a concentration level of the controlling dye liquor that is a measurement object.

2. An automatic color-tone test device set forth in claim 1, wherein an internal space of the measurement cell is divided into two liquid-tight independent spaces mutually different in light transmission distance, and one of the independent spaces has a light transmission distance of 10–50 times that of the other of the independent spaces.

3. An automatic color-tone test device set forth in claim 1, wherein the spectrophotometer comprises a photodiode array.

4. An automatic controlling system for dye liquor, comprising:

an automatic controlling device having one or plural dye liquor tank(s) filled with dye liquor, a water tank filled with water, a mixer for mixing the liquor fed from each of the tanks, and one or plural flow rate control device (s) for controlling a flow rate of the liquor fed into the mixer from each of the tanks;

an automatic color-tone test device set forth in claim 1; and a control computer section which performs a component analysis on the basis of operation judgment results of the statistical test computer section of the automatic color-tone test device so as to control the flow rate control device on the basis of the analysis results;

wherein at least a part of the controlling dye liquor fed through the mixer of the automatic controlling device is introduced into the dye liquor introduction tube of the automatic color-tone test device.

5. An automatic controlling system for dye liquor set forth in claim 4, wherein the flow rate control device for controlling a flow rate of the liquor fed into the mixer from the dye liquor tank comprises:

a main conduit having at one end a suction port and at another end a discharge port;

a pump provided in the main conduit and having a predetermined discharge flow rate range;

a bypass conduit branched from a position of more discharge port side than the pump in the main conduit and reaching the discharge port; and flow meter and regulation valve which are provided in the bypass conduit;

wherein a control flow rate range of the regulation valve includes a flow rate range of lower flow rate side than a predetermined discharge flow rate range of the pump, and an opening adjustment of the regulation valve is performed on the basis of a measurement value detected by the flow meter.

6. An automatic controlling system for dye liquor set forth in claim 5, wherein there is provided a return conduit for communication-connecting a position from the pump in the conduit of the flow rate control device to the flow meter and a position of more suction port side than the pump in the main conduit.

* * * * *